United States Patent [19]

Arlt et al.

[11] 4,386,082
[45] May 31, 1983

[54] PESTICIDALLY ACTIVE PHOSPHORIC (PHOSPHONIC) ACID ESTER AMIDES

[75] Inventors: Dieter Arlt, Cologne; Bernhard Homeyer, Leverkusen; Ingeborg Hammann, Cologne; Volker Paul, Solingen, all of Fed. Rep. of Germany

[73] Assignee: Bayer Aktiengesellschaft, Leverkusen, Fed. Rep. of Germany

[21] Appl. No.: 352,687

[22] Filed: Feb. 26, 1982

[30] Foreign Application Priority Data

Mar. 18, 1981 [DE] Fed. Rep. of Germany ....... 3110595

[51] Int. Cl.³ .................... A01N 57/28; C07F 9/24
[52] U.S. Cl. .................................... 424/215; 260/947
[58] Field of Search ................. 260/947; 424/215

[56] References Cited

U.S. PATENT DOCUMENTS 3,755,507 8/1973 Brown et al. .................. 260/947

FOREIGN PATENT DOCUMENTS 1053 3/1979 European Pat. Off. .
1022587 1/1958 Fed. Rep. of Germany ...... 260/947
2629016 1/1978 Fed. Rep. of Germany .
2904927 8/1980 Fed. Rep. of Germany ...... 260/947

*Primary Examiner*—Anton H. Sutto
*Attorney, Agent, or Firm*—Sprung, Horn, Kramer & Woods

[57] ABSTRACT

The invention relates to new phosphoric (phosphonic) acid ester amides of the general formula

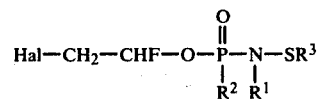 (I)

wherein
$R^1$ represents a hydrogen atom or an optionally substituted alkyl radical,
$R^2$ represents an optionally substituted alkyl or optionally substituted alkoxy radical,
$R^3$ represents an optionally substituted alkyl or optionally substituted aryl radical and
Hal represents a halogen atom, which are obtained by the reaction of phosphoric (phosphonic) acid ester amides of the general formula

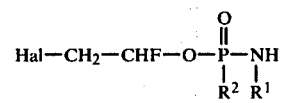 (II)

wherein $R^1$, $R^2$ and Hal have the meaning given above, with sulphenyl chlorides of the general formula

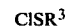 (III)

wherein $R^3$ has the meaning given above, in the presence of an acid acceptor and, if appropriate, in the presence of a solvent, and which can be used for combating pests (such as insects, acaricids and nematodes) or for combating microbes (especially fungi).

13 Claims, No Drawings

PESTICIDALLY ACTIVE PHOSPHORIC (PHOSPHONIC) ACID ESTER AMIDES

The invention relates to certain new O-(1-fluoro-2-halogeno-ethyl)-phosphoric (phosphonic) acid ester amides, to a process for their production and to their use as agents for combating pests and fungi, especially as insecticides, nematicides and fungicides.

It has already been disclosed in U.S. Pat. No. 4,159,324 that certain phosphoric (phosphonic) ester amides have insecticidal, acaricidal and nematicidal properties. However, these compounds are not always completely satisfactory under certain conditions of use.

The present invention now provides, as new compounds, the phosphoric (phosphonic) acid ester amides of the general formula

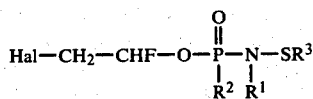 (I)

wherein
R$^1$ represents a hydrogen atom or an optionally substituted alkyl radical,
R$^2$ represents an optionally substituted alkyl or optionally substituted alkoxy radical,
R$^3$ represents an optionally substituted alkyl or optionally substituted aryl radical and
"Hal" represents a halogen atom.

According to the present invention we further provide a process for the production of a compound of the present invention characterized in that a phosphoric (phosphonic) acid ester amide of the general formula

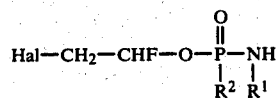 (II)

wherein R$^1$, R$^2$ and "Hal" have the meaning given above, is reacted with a sulphenyl chloride of the general formula $$ClSR^3 \quad (III)$$

wherein R$^3$ has the meaning given above, in the presence of an acid acceptor and, if appropriate, in the presence of a solvent.

Surprisingly, the new compounds of the present invention are distinguished in comparison to the already known corresponding compounds in particular by a low level of toxicity to warm-blooded animals and particularly by a specific activity as a systemic soil insecticide of long duration of action. In addition, the compounds according to the invention are very well tolerated by plants and also fungicidally active.

The optionally substituted alkyl radicals of R$^1$, R$^2$ and R$^3$, preferably represent straight-chain or branced alkyl having 1 to 6, especially 1 to 4, carbon atoms. Optionally substituted methyl, ethyl, n-propyl, i-propyl, n-butyl, i-butyl, s-butyl and t-butyl may be mentioned as examples.

The optionally substituted alkoxy radical of R$^2$ preferably represents a straight-chain or branched alkoxy radical having preferably 1 to 6, especially 1 to 4 carbon atoms. Optionally substituted methoxy, ethoxy, n-propoxy, i-propoxy, n-butoxy, i-butoxy, s-butoxy and t-butoxy may be mentioned as examples.

The alkyl radicals of R$^1$, R$^2$ and R$^3$, as well as the alkoxy radical of R$^2$, can carry one or several, preferably 1 to 3, especially 1 or 2, identical or different substituents. The following may be quoted as examples of substituents: alkoxy having preferably 1 to 4, especially 1 or 2 carbon atoms (such as methoxy, ethoxy, n-propoxy, i-propoxy, n-butoxy, i-butoxy and t-butoxy), alkylthio having preferably 1 to 4, especially 1 or 2 carbon atoms (such as methylthio, ethylthio, n-propylthio, i-propylthio, n-butylthio, i-butylthio and t-butylthio); halogen (preferably fluorine, chlorine, bromine and iodine, especially chlorine and bromine) and cyano.

Halogen-substituted alkyl (halogenoalkyl) and alkoxy (halogenoalkoxy) may be mentioned as preferred substituted alkyl radicals of R$^1$ and R$^3$ and alkoxy radical R$^2$, respectively. A halogenoalkyl radical of R$^3$ preferably contains 1 to 4, especially 1 or 2, carbon atoms and preferably 1 to 5, especially 1 to 3, identical or different halogen atoms (such as fluorine, chlorine, bromine and iodine, preferably fluorine and/or chlorine).

The halogen atom "Hal" preferably represents fluorine, chlorine, bromine and iodine, particularly chlorine and bromine.

The optionally substituted aryl radical of R$^3$ preferably represents an aryl radical having 6 or 10 carbon atoms in the aryl part. Optionally substituted phenyl or naphthyl, particularly phenyl, may be mentioned as examples.

The aryl radical of R$^3$ can carry one or several, preferably 1 to 3, especially 1 or 2, identical or different substituents. The following may be quoted as examples of substituents: alkyl having preferably 1 to 4, especially 1 or 2, carbon atoms (such as methyl, ethyl, n-propyl, 1-propyl, n-butyl, i-butyl and t-butyl); alkoxy having preferably 1 to 4, especially 1 or 2, carbon atoms (such as methoxy, ethoxy, n-propoxy, i-propoxy, n-butoxy, i-butoxy and t-butoxy); alkylthio having preferably 1 to 4, especially 1 or 2, carbon atoms, (such as methylthio, ethylthio, n-propylthio, i-propylthio, n-butylthio, i-butylthio and t-butylthio); halogenoalkyl having preferably 1 to 4, especially 1 or 2, carbon atoms and preferably 1 to 5, particularly 1 to 3, halogen atoms, the halogen atoms being identical or different and preferably representing fluorine, chlorine or bromine, especially fluorine, (such as trifluoromethyl); halogen, preferably fluorine, chlorine, bromine and iodine, especially chlorine and bromine; cyano or nitro. Phenyl which is substituted by 1 to 3 fluorine atoms, chlorine atoms or bromine atoms, preferably chlorine atoms or fluorine atoms, may be particularly mentioned (halogenophenyl).

Preferred compounds of the present invention are those compounds where
R$^1$ represents a hydrogen atom or an alkyl radical,
R$^2$ represents an alkyl or alkoxy radical,
R$^3$ represents an alkyl, halogenoalkyl or halogenophenyl radical and
Hal represents a chlorine or bromine atom.

Particularly preferred compounds of the present invention are those compounds wherein
R$^1$ represents a hydrogen atom or a C$_{1-4}$-alkyl radical,
R$^2$ represents a C$_{1-4}$-alkyl or C$_{1-4}$-alkoxy radical,
R$^3$ represents a C$_{1-4}$-alkyl, C$_{1-4}$-halogenoalkyl or halogenophenyl radical and Hal represents a chlorine or bromine atom.

Very particularly preferred compounds of the formula (I) are those compounds wherein $R^1$ represents a hydrogen atom or a methyl, ethyl, i-propyl, n-propyl, 1-chloroisopropyl or secl-butyl radical, $R^2$ represents a $C_{1-4}$-alkyl or $C_{1-4}$-alkoxy radical, and $R^3$ represents a $CCl_3$-, $CFCl_2$-, $CF_3$-, phenyl, o-chlorophenyl, m-chlorophenyl or p-chlorophenyl radical.

If, for example, O-(1-fluoro-2-chloro-ethyl)-O-methyl-phosphoric acid diester N-ethyl-amide and dichlorofluoromethanesulphenyl chloride are used as the starting materials, the reaction according to the present invention is illustrated by the following equation:

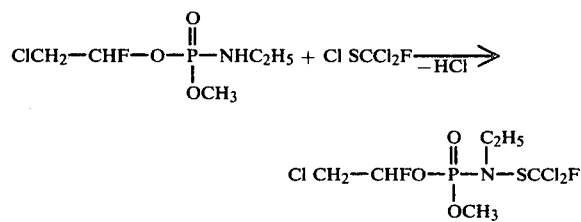

O-(1-Fluoro-2-halogenoethyl)-phosphoric (phosphonic) acid ester amides of formula (II) used as the starting materials are known and can be prepared in a customary manner according to known processes.

The following may be mentioned as examples of these starting materials: methane- and ethane-O-(1-fluoro-2-chloro-ethyl)-phosphonic acid ester amide, methane- and ethane-O-(1-fluoro-2-bromo-ethyl)-phosphonic acid ester amide, and the N-alkyl derivatives thereof, having 1 to 4 carbon atoms, and also O-(1-fluoro-2-chloro-ethyl)-O-methyl-phosphoric acid diester amide, O-(1-fluoro-2-chloro-ethyl)-O-methyl-phosphoric acid diester N-ethylamide, O-(1-fluoro-2-chloro-ethyl)-O-methyl-phosphoric acid diester N-methylamide, O-(1-fluoro-2-chloro-ethyl)-O-methyl-phosphoric acid diester N-i-propyl-amide, O-(1-fluoro-2-chloro-ethyl)-O-methyl-phosphoric acid diester N-n-propyl-amide, O-(1-fluoro-2-chloro-ethyl)-O-methyl-phosphoric acid diester N-sec.-butyl-amide, O-(1-fluoro-2-chloro-ethyl)-O-ethyl-phosphoric acid diester amide, O-(1-fluoro-2-chloro-ethyl)-O-ethyl-phosphoric acid diester N-ethyl-amide, O-(1-fluoro-2-chloro-ethyl)-O-ethyl-phosphoric acid diester N-methyl-amide, O-(1-fluoro-2-chloro-ethyl)-O-ethyl-phosphoric acid diester N-i-propyl-amide, O-(1-fluoro-2-chloro-ethyl)-O-ethyl-phosphoric acid diester N-n-propyl-amide, O-(1-fluoro-2-chloro-ethyl)-O-ethyl-phosphoric acid diester N-sec.-butyl-amide, O-(1-fluoro-2-chloro-ethyl)-O-i- or n-propyl phosphoric acid diester amide, O-(1-fluoro-2-chloro-ethyl)-O-i- or n-propyl phosphoric acid diester N-ethyl-amide, O-(1-fluoro-2-chloro-ethyl)-O-i- or n-propyl phosphoric acid diester N-methyl-amide, O-(1-fluoro-2-chloro-ethyl)-O-i- or n-propyl phosphoric acid diester N-i-propyl-amide, O-(1-fluoro-2-chloro-ethyl)-O-i- or n-propyl phosphoric acid diester N-n-propyl-amide, O-(1-fluoro-2-chloro-ethyl)-O-i- or n-propyl phosphoric acid diester N-sec.-butyl-amide, O-(1-fluoro-2-bromo-ethyl)-O-methyl-phosphoric acid diester amide, O-(1-fluoro-2-bromo-ethyl)-O-methyl-phosphoric acid diester N-ethyl-amide, O-(1-fluoro-2-bromo-ethyl)-O-methyl-phosphoric acid diester N-methyl-amide, O-(1-fluoro-2-bromo-ethyl)-O-methyl-phosphoric acid diester N-i-propyl-amide, O-(1-fluoro-2-bromo-ethyl)-O-methyl-phosphoric acid diester N-n-propyl-amide, O-(1-fluoro-2-bromo-ethyl)-O-methyl-phosphoric acid diester N-sec.-butyl-amide, O-(1-fluoro-2-bromo-methyl)-O-ethyl-phosphoric acid diester N-amide, O-(1-fluoro-2-bromo-ethyl)-O-ethyl-phosphoric acid N-ethyl-amide, O-(1-fluoro-2-bromo-ethyl)-O-ethyl-phosphoric acid N-methyl-amide, O-(1-fluoro-2-bromo-ethyl)-O-ethyl-phosphoric acid diester N-i-propyl-amide, O-(1-fluoro-2-bromo-ethyl)-O-ethyl-phosphoric acid diester N-n-propyl-amide, O-(1-fluoro-2-bromo-ethyl)-O-ethyl-phosphoric acid diester N-sec.-butyl-amide and O-(1-fluoro-2-bromo-ethyl)-O-ethyl-phosphoric acid diester N-chloro-isopropyl-amide.

The reaction of the stated starting materials of the formulae (II) and (III) to give the compounds of the formula (I) according to the invention is preferably carried out with the concomitant use of suitable solvents and diluents. Virtually any of the inert organic solvents are suitable solvents and diluents. These include, in particular, aliphatic and aromatic, optionally chlorinated hydrocarbons (such as benzene, toluene, xylene, benzine, methylene chloride, chloroform, carbon tetrachloride or chlorobenzene), or ethers (for example diethyl ether, dibutyl ether or dioxane) or ketones (for example acetone, methyl ethyl ketone, methyl isopropyl ketone and methyl isobutyl ketone) as well as nitriles (such as acetonitrile and propionitrile).

Any of the customary acid-binding agents can be used as the acid acceptors; tertiary amines (such as trimethylamine, triethylamine, dimethylaniline, dimethylbenzylamine and pyridine) or alkali metal carbonates (such as sodium carbonate and potassium carbonate) have proved particularly suitable.

The reaction temperature can be varied within a relatively wide range. In general, the reaction is carried out at a temperature between 0° and 100° C., preferably at a temperature between 20° and 40° C. In general, the reaction is allowed to proceed under normal pressure.

The reactants are preferably employed in an equimolar ratio. An excess of one or the other of the components has no substantial advantages. The reaction is preferably carried out in one of the solvents given, in the presence of an acid acceptor. The working-up of the mixture is effected, according to customary methods, by filtering, washing the filtrate and distilling off the solvent.

The new compounds are obtained in the form of oils, which cannot be distilled without decomposition, but can be freed from the last volatile constituents by so-called "incipient distillation", that is to say by prolonged heating to moderately elevated temperature under reduced pressure, and can be purified in this manner. They are characterized by their refractive indices.

The active compounds are well tolerated by plants, have a favorable level of toxicity to warm-blooded animals, and are suitable for combating arthropod pests, especially insects and arachnida, and nematodes, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella,* Agrotis spp., Euxoa spp., Feltia spp., *Earias insulana, Heliothis* spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chyrsocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicelphalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

Furthermore, the active compounds according to the invention have a powerful microbicidal, particularly fungicidal, action and can be employed in practice for combating undesired micro-organisms. The active compounds are suitable for use as plant protection agents.

Fungicidal agents in plant protection are employed for combating Plasmodiophoromycetes, Oomycetes, Chyrtridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The following may be mentioned as examples of micro-organisms which can be combated: *Fusarium nivale, Rhizoctomia solani, Cochliobolus miyabeanus, Botrytis cinera, Pyricularia oryzae, Helminthosporium gramineum, Phytophtora cactorum, Phythium ultimum* and *Pelicularia saskii.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepated from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The present invention also provides a pesticidal and microbicidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids, and nematodes) and microbes (especially fungi) which comprises applying to the pests or microbes, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The examples which follow illustrate the preparation of the compounds according to the invention:

EXAMPLE 1

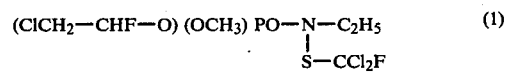

$(ClCH_2-CHF-O)(OCH_3)PO-N-C_2H_5 \quad (1)$
$\qquad\qquad\qquad\qquad\qquad\quad |$
$\qquad\qquad\qquad\qquad\qquad S-CCl_2F$ 21.0 g of O-(1-fluoro-2-chloro-ethyl)-O-methyl-phosphoric acid diester N-ethyl-amide and 20.0 g (0.12 mol) of dichlorofluoromethanesulphenyl chloride were dissolved in 150 ml of toluene. 12.0 (0.12 mol) of triethylamine were added dropwise to the solution at 20° to 25° C., while stirring. After 5 hours, the reaction mixture was extracted with twice 500 ml of water, and the organic phase was separated off and dried with sodium sulphate. The toluene was removed in a rotary evaporator, under the vacuum from an oil pump. 29.5 g of N-[O-(1-fluoro-2-chloro-ethyl)-O-methyl-phosphoryl]-N-ethyl-dichlorofluoromethane-sulphenamide, $n_D^{20}$: 1.4879, were obtained.

EXAMPLE 2

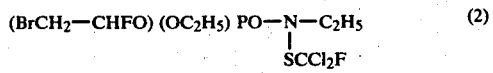

27.8 g (0.1 mol) of O-(1-fluoro-2-bromo-ethyl)-O-ethyl-phosphoric acid diester N-ethyl-amide and 20.0 g (0.12 mol) of dichlorofluoromethanesulphenyl chloride were dissolved in 150 ml of toluene. 12.0 g (0.12 mol) of triethylamine were added dropwise to the solution at 20°-25° C., while stirring. After 5 hours, the reaction mixture was extracted with twice 500 ml of water, and the organic phase was separated off and dried with sodium sulphate. The toluene was removed in a rotary evaporator, under the vacuum from an oil pump. 37.5 g of N-[O-(1-fluoro-2-bromo-ethyl)-O-ethyl-phosphoryl]-N-ethyl-dichlorofluoro-methanesulphenamide, $n_D^{20}$: 1.4895, were obtained.

The following compounds were synthesized in a manner analogous to that described in Example 1 or 2, and were characterized by their refractive indices:

3 (ClCH$_2$—CHF—O) (OC$_2$H$_5$) PO—N—C$_2$H$_5$  $n_D^{20}$:1.4725
　　　　　　　　　　　　　　　　　|
　　　　　　　　　　　　　　　　SCCl$_2$F 4 (ClCH$_2$—CHF—O) (OC$_2$H$_5$) PO—N—CH$_3$  $n_D^{20}$:1.4739
　　　　　　　　　　　　　　　　　|
　　　　　　　　　　　　　　　　SCCl$_2$F

CH$_3$  $n_D^{20}$:1.4807
　　　　　　　　　　　　　　　　　|
5 (BrCH$_2$—CHF—O) (OC$_2$H$_5$) PO—N—CH—C$_2$H$_5$
　　　　　　　　　　　　　　　　　|
　　　　　　　　　　　　　　　　SCCl$_2$F 6 (ClCH$_2$—CHF—O) (OCH$_3$) PO—N—CH(CH$_3$)$_2$  $n_D^{20}$:1.4718
　　　　　　　　　　　　　　　　　|
　　　　　　　　　　　　　　　　SCCl$_2$F

The pesticidal activity of the compounds of this invention is illustrated by the following examples wherein the compounds according to the present invention are each identified by the number (given in brackets) from examples hereinabove:

The known comparison compounds are identified as follows:

O-(1-fluoro-2-bromoethyl)-O-ethyl-phosphoric acid diester N-ethylamide ("Comparison Compound A") known from DE-Offenlegungsschrift (German Published Specification) issued to U.S. Pat. No. 4,159,324 and O-(1-fluoro-2-chloroethyl)-O-ethyl-phosphoric acid diester N-methylamide ("Comparison Compound B").

EXAMPLE 3

Critical concentration test/soil inects

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test animals were introduced into the treated soil, and after 2 days the degree of effectiveness of the active compound was determined in % by counting the dead and live test insects. The degree of effectiveness was 100% if all the test insects had been killed and was 0% if just as many test insects were still alive as in the case of the untreated control.

In a test at a concentration of 1.25 ppm, the "Comparison Compound A" showed no action (0%), while the compounds (1), (2), (3) and (4) showed a degree of destruction of 100%.

EXAMPLE 4

Critical concentration test/root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of an active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The treated soil was filled into pots and these were planted with cabbage (*Brassica oleracea*). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation was made by counting or estimating the dead insects. The root-systemic action of the active compound was deduced from the mortality figures. It was 100% if all the test insects had been killed and 0% if just as many test insects were still alive as in the case of the untreated control.

In this test, the compounds (1), (2), (3) and (4), for example, showed a degree of destruction of 100% at a concentration of 1.25 ppm.

EXAMPLE 5

Critical concentration test/nematodes

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amont of emulsifier was added and the concentrate was diluted with water to the desired concentration.

The preparation of active compound was intimately mixed with soil which is heavily infested with the test nematodes. The concentration of the active compound in the preparation was of practically no importance, only the amount of active compound per unit volume of soil, which was given in ppm, being decisive. The treated soil was filled into pots, lettuce was sown-in and the pots were kept at a greenhouse temperature of 27° C.

After four weeks, the lettuce roots were examined for infestation with nematodes (root galls), and the degree of effectiveness of the active compound was determined in %. The degree of effectiveness was 100% if infestation was completely avoided and was 0% if the infestation was just as high as in the case of the control plants in untreated soil which had been infested in the same manner.

In a test at 5 ppm, the compounds (1) and (2), for example, showed a degree of destruction of 100%.

EXAMPLE 6

Drosophila test

Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

1 cm$^3$ of the preparation of the active compound was pipetted onto a filter paper disc (7 cm diameter). The wet disc was placed over the opening of a glass vessel containing 50 vinegar flies (*Drosophilia melanogaster*) and was covered with a glass plate.

After the specified periods of time, the destruction in % was determined. 100% meant that all the flies had been killed; 0% meant that none of the flies had been killed.

In a test at a concentration of 0.001%, the Comparison Compounds A and B showed no action (0%) after 1 day, while the compounds (1), (3) and (4) showed a degree of destruction of 100%.

EXAMPLE 7

Tetranychus test (resistant)

Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, the "Comparison Compound A", at a concentration of 0.1%, showed a degree of destruction of 40% after 2 days, while the compounds (1), (2), (3), (4) and (5) showed a degree of destruction of 100%.

EXAMPLE 8

Agar plate test (antimicrobial action)

Nutrient medium used:
  39 parts by weight of potato decoction
  5 parts by weight of agar agar
  10 parts by weight of peptone and
  5 parts by weight of malt
  dissolved in 1,000 ml of distilled water, the solution being kept in an autoclave at 121° C. for 30 minutes.

Solvent: 2 parts by weight of water
Ratio of the amounts of solvent to nutrient medium: 2:100.

To produce a suitable preparation of active compound, 1 part by weight of active compound was mixed with the stated amount of solvent.

The concentrate was thoroughly mixed, in the stated proportion, with the liquid nutrient medium and the mixture was then poured into Petri dishes.

When the nutrient medium had cooled and solidified, the plates were inoculated with the following microorganisms and were incubated at about 21° C.: *Fusarium nivale, Rhizoctomia solani, Cochliobolus miyabenus, Botrytis cinerea, Pyricularia oryzae, Helminthosprium gramineum, Phytophthora cactorum, Pythium ultimum* and *Pelicularia sasakii.*

Evaluation was carried out after 2 to 8 days, depending on the speed of growth of the micro-organisms. The inhibition of growth was used as a measure (with ratings 1 to 10) of the action of the preparations, the rating 10 representing no inhibition and the rating 1 representing a very good inhibition.

In a test at an active compound concentration of 10 ppm, for example with *Furarium nivale* and *Rhizoctonia solani,* the known fungicidal active compound "Zineb" gave arating of 9, whilst the compounds (1), (2), (3) and (4), for example, obtained a rating of 1. Similarly favorable results were also achieved using the remaining abovementioned microbes.

It will be appreciated that the instant specification and examples are set forth by way of illustration and not limitation, and that various modifications and changes may be made without departing from the spirit and scope of the present invention.

We claim:

1. A phosphoric (phosphonic) acid ester amide of the formula $$Hal-CH_2-CHF-O-\underset{R^2}{\underset{|}{P}}(=O)-\underset{R^1}{\underset{|}{N}}-SR^3$$

in which
  $R^1$ is a hydrogen atom or an optionally substituted alkyl radical,
  $R^2$ is an optionally substituted alkyl or optionally substituted alkoxy radical,
  $R^3$ is an optionally substituted alkyl or optionally substituted aryl radical, and
  Hal is a halogen atom.

2. A method of combating pests or microbes comprising applying to the pests or microbes or to a habitat thereof, a pesticidally or microbicidally effective amount of a compound according to claim 1.

3. The method according to claim 2, wherein such compound is
- N-[O-(1-fluoro-2-chloro-ethyl)-O-methyl-phosphoryl]-N-ethyl dichlorofluoromethane-sulphenamide,
- N-[O-(1-fluoro-2-bromo-ethyl)-O-ethyl-phosphoryl]-N-ethyl-dichlorofluoromethane-sulphenamide,
- N-[O-(1-fluoro-2-chloro-ethyl)-O-ethyl-phosphoryl]-N-ethyl-dichlorofluoromethane-sulphenamide,
- N-[O-(1-fluoro-2-chloro-ethyl)-O-ethyl-phosphoryl]-N-methyl-dichlorofluoromethane-sulphenamide,
- N-[O-(1-fluoro-2-bromo-ethyl)-O-ethyl-phosphoryl]-N-sec.-butyl-dichlorofluoromethane-sulphenamide or
- N-[O-(1-fluoro-2-chloro-ethyl)-O-methyl-phosphoryl]-N-isopropyl-dichlorofluoromethane-sulphenamide.

4. A compound according to claim 1, in which
$R^1$ is a hydrogen atom or an alkyl radical,
$R^2$ is an alkyl or alkoxy radical,
$R^3$ is an alkyl, halogenoalkyl or halogenophenyl radical, and
Hal is a chlorine or bromine atom.

5. A compound according to claim 1, in which
$R^1$ is a hydrogen atom or a $C_{1-4}$-alkyl radical,
$R^2$ is a $C_{1-4}$-alkyl or $C_{1-4}$-alkoxy radical,
$R^3$ is a $C_{1-4}$-alkyl, $C_{1-4}$-halogenoalkyl or halogenophenyl radical, and
Hal is a chlorine or bromine atom.

6. A compound according to claim 1, in which
$R^1$ is a hydrogen atom, or a methyl, ethyl, i-propyl, n-propyl, 1-chloroisopropyl or sec-butyl radical,
$R^2$ is a $C_{1-4}$-alkyl or $C_{1-4}$-alkoxy radical, and
$R^3$ is a $CCl_3$-, $CFCl_2$-, $CF_3$-, phenyl, o-chlorophenyl, m-chlorophenyl or p-chlorophenyl radical.

7. A compound according to claim 1, wherein such compound is N-[O-(1-fluoro-2-chloro-ethyl)-O-methyl-phosphoryl]-N-ethyl-dichlorofluoromethane-sulphenamide of the formula

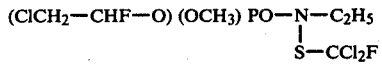

8. A compound according to claim 1, wherein such compound is N-[O-(1-fluoro-2-bromo-ethyl)-O-ethyl-phosphoryl]-N-ethyl-dichlorofluoromethane-sulphenamide of the formula

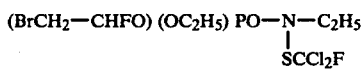

9. A compound according to claim 1, wherein such compound is N-[O-(1-fluoro-2-chloro-ethyl)-O-ethyl-phosphoryl]-N-ethyl-dichlorofluoromethane-sulphenamide of the formula

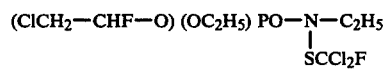

10. A compound according to claim 1, wherein such compound is N-[O-(1-fluoro-2-chloro-ethyl)-O-ethyl-phosphoryl]-N-methyl-dichloromethane-sulphenamide of the formula

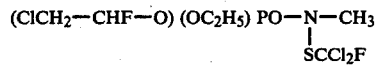

11. A compound according to claim 1, wherein such compound is N-[O-(1-fluoro-2-bromo-ethyl)-O-ethyl-phosphoryl]-N-sec.-butyl-dichlorofluoromethane-sulphenamide of the formula

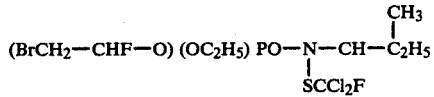

12. A compund according to claim 1, wherein such compound is N-[O-(1-fluoro-2-chloro-ethyl)-O-methyl-phosphoryl]-N-isopropyl-dichlorofluoromethane-sulphenamide of the formula

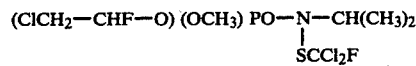

13. A pesticidal or microbicidal composition, comprising a pesticidally or microbicidally effective amount of a compound according to claim 1 in admixture with a diluent.

* * * * *